US008335557B2

(12) United States Patent
Maschke

(10) Patent No.: US 8,335,557 B2
(45) Date of Patent: Dec. 18, 2012

(54) SYSTEM FOR CARRYING OUT AND MONITORING MINIMALLY-INVASIVE INTERVENTIONS

(75) Inventor: Michael Maschke, Lonnerstadt (DE)

(73) Assignee: Siemens Aktiengesellschaft, München (DE)

( * ) Notice: Subject to any disclaimer, the term of this patent is extended or adjusted under 35 U.S.C. 154(b) by 1397 days.

(21) Appl. No.: 12/004,364

(22) Filed: Dec. 20, 2007

(65) Prior Publication Data

US 2008/0247506 A1 Oct. 9, 2008

(30) Foreign Application Priority Data

Dec. 22, 2006 (DE) .......................... 10 2006 061 178

(51) Int. Cl.
*A61B 5/05* (2006.01)
(52) U.S. Cl. .......................... 600/427; 600/407; 378/117
(58) Field of Classification Search ........... 600/407–480
See application file for complete search history.

(56) References Cited

U.S. PATENT DOCUMENTS

| 5,365,926 | A | | 11/1994 | Desai | |
|---|---|---|---|---|---|
| 5,409,000 | A | | 4/1995 | Imran | |
| 5,646,525 | A | | 7/1997 | Gilboa | |
| 5,654,997 | A | * | 8/1997 | Brownell et al. ............. | 378/117 |
| 5,706,416 | A | | 1/1998 | Mann et al. | |
| 5,805,664 | A | * | 9/1998 | Whipple et al. ............. | 378/117 |
| 6,015,414 | A | * | 1/2000 | Werp et al. .................... | 606/108 |
| 6,038,468 | A | | 3/2000 | Rex | |
| 6,148,823 | A | | 11/2000 | Hastings | |
| 6,272,368 | B1 | * | 8/2001 | Alexandrescu ............... | 600/407 |
| 6,408,051 | B2 | * | 6/2002 | Habraken et al. ............. | 378/117 |
| 6,456,684 | B1 | * | 9/2002 | Mun et al. ....................... | 378/20 |
| 6,506,972 | B1 | | 1/2003 | Wang | |
| 6,556,695 | B1 | | 4/2003 | Packer et al. | |
| 6,637,266 | B1 | * | 10/2003 | Froom ............................ | 73/583 |
| 6,738,673 | B2 | | 5/2004 | Desai | |

(Continued)

FOREIGN PATENT DOCUMENTS

DE 3636678 A1 5/1988

(Continued)

OTHER PUBLICATIONS

Siemens Medical Solutions; AXIOM Sensis—Hemodynamic and Electrophysiology Information and Recording System for Cardiac Cathlabs; © 2005 Siemens Medical Solutions, pp. 1-11, Order No. A91001-M1400-G907-4-7600, AX CRM NA 02053; Others; 2005.

(Continued)

*Primary Examiner* — Brian Casler
*Assistant Examiner* — Nasir S Shahrestani

(57) ABSTRACT

There is described a system for carrying out and monitoring minimally-invasive interventions with an x-ray device, in which at least one x-ray emitter and a x-ray detector are attached to one or more robot arms of one or more multi-axis articulated-arm robots, with which they are able to be moved for recording images from different projection directions on a predeterminable path around a patient support facility. The system includes a control and evaluation unit with interfaces for catheters and devices for carrying out the minimally-invasive intervention. The control and evaluation unit is embodied for the processing of measurement and/or image data which it receives from the catheters and devices and for control of the catheters and devices for recording the measurement and/or image data. With the proposed system the workflow is covered completely and seamlessly from the examination to the therapy, especially in the treatment of tachycardial arrythmias.

19 Claims, 2 Drawing Sheets

U.S. PATENT DOCUMENTS

| | | | |
|---|---|---|---|
| 6,772,001 | B2 | 8/2004 | Maschke |
| 6,804,656 | B1 * | 10/2004 | Rosenfeld et al. ............ 705/3 |
| 6,869,217 | B2 * | 3/2005 | Rasche et al. ............ 378/197 |
| 7,066,291 | B2 * | 6/2006 | Martins et al. ............ 180/167 |
| 7,607,440 | B2 * | 10/2009 | Coste-Maniere et al. .... 128/898 |
| 7,933,641 | B2 * | 4/2011 | Maschke et al. ............ 600/427 |
| 2002/0049375 | A1 * | 4/2002 | Strommer et al. ............ 600/407 |
| 2002/0181645 | A1 | 12/2002 | Bruder et al. |
| 2003/0040674 | A1 | 2/2003 | Corl et al. |
| 2003/0199748 | A1 | 10/2003 | Camus et al. |
| 2003/0220561 | A1 | 11/2003 | Camus |
| 2004/0008882 | A1 | 1/2004 | Hornegger et al. |
| 2005/0058248 | A1 | 3/2005 | Klingenbeck-Regn |
| 2005/0085714 | A1 * | 4/2005 | Foley et al. ............ 600/424 |
| 2005/0256398 | A1 * | 11/2005 | Hastings et al. ............ 600/423 |

FOREIGN PATENT DOCUMENTS

| | | |
|---|---|---|
| DE | 4436828 C1 | 3/1996 |
| DE | 10210645 A1 | 10/2003 |
| DE | 10210646 A1 | 10/2003 |
| DE | 10210648 A1 | 10/2003 |
| DE | 10255957 A1 | 8/2004 |
| DE | 10210650 B4 | 4/2005 |
| DE | 102004057308 A1 | 7/2006 |
| DE | 102005012700 A1 | 9/2006 |
| DE | 102005030609 A1 | 1/2007 |
| DE | 102005032755 A1 | 1/2007 |
| EP | 0220501 B1 | 5/1989 |
| EP | 0885594 B1 | 4/2003 |
| WO | WO 0043730 A1 | 7/2000 |
| WO | WO 0111409 A2 | 2/2001 |

OTHER PUBLICATIONS

Biophan Technologies Inc.; MRI Shielding for Medical Devices; pp. 1-5, http://www.biophan.com/shielding.php.

Biosense Webster; Carto XP EP Navigation; pp. 1-3, 1-4,http://www.jnjgateway.com/home.jhtml?loc=USENG&page=viewContent&contentId=09008b988008e25c&nodekey=/Prod_Info/Company/Biosense_Webster/Electrophysiology/EP_Navigation_Systems; Others; 2005.

Patrick Kurp; AXIOM Artis FD Systems DynaCT—A Breakthrough in Interventional 3D Imaging Kurp; Reprint from Medical Solutions, Jan. 2005, p. 46-51; 2005.

Boston Scientific Corporation; RPM™ Realtime Position Management® System; http://www.bostonscientific.com/med_specialty/deviceDetail.jsp?task=tskBasicDevice.jsp&sectionId=4&relId=1,20,21,22&deviceId=470&uniqueId=MPDB132 und http://www.bostonscientific.com/common_templates/singleDetailList.jsp?task=tskDeviceStatement.jsp&sectionId=4&relId=1,20,21,32,33&deviceId=470; 2005.

Osypka Medical GMBH; AESCULON® Window to the Circulation®; http://www.aesculon.de/index.html und http://www.osypkamed.de/3_1.html.

Hansen Medical; Technology Advantages and System Overview The Sensei Robotic Catheter System Hansen Medical; http://www.hansenmedical.com/advantages.aspx und http://www.hansenmedical.com/system.aspx.

Fred H.M. Wittkampf, Eric F.D. Wever, Richard Derksen, Arthur A.M. Wilde, Hemanth Ramanna, Richard N.W. Hauer, Etienne O. Robles De Medina; American Heart Association "LocaLisa—New Technique for Real-Time 3-Dimensional Localization of Regular Intracardiac Electrodes"; Circulation 1999;99;1312-1317; Magazine; 1999.

Endocardial Solutions, Inc.; "Endocardial Solutions Announces First Successful Human NAVEX Procedure"; pp. 1-2, http://www.endocardialsolutions.com/investor/2002_08_14.html; 2002.

Siemens AG, Medical Solutions; AXIOM Artis FC/BC—The Heart of Your Cardiology Department (with CATHCOR); Ord.-No. A91100-M1400-F659-01-7600 BKW 62659 WS 05015.; 2005; pp. 1-18.

* cited by examiner

SYSTEM FOR CARRYING OUT AND MONITORING MINIMALLY-INVASIVE INTERVENTIONS

CROSS REFERENCE TO RELATED APPLICATIONS

This application claims priority of German application No. 10 2006 061 178.0 DE filed Dec. 22, 2006, which is incorporated by reference herein in its entirety.

FIELD OF INVENTION

The present invention relates to a system for carrying out and monitoring minimally-invasive interventions, especially for treatment of electrophysiological diseases. Among the most serious cardiological diseases are the tachycardial arrhythmias, such as atrial fibrillation for example. In this case conduction pathway disturbances in the heart mean that the atrium is excited at high frequency. With other, for example ventricular tachycardias, there is no complete contraction and the result is thus an insufficient pumping power of the heart. In the past attempts were either made to reduce the effect of atrial fibrillation by taking medicines continuously or to remedy the cause of the atrial fibrillation by a heart operation in which the cardiac conducting tissue was severed in specific parts of the atrium. This surgical treatment however has a relatively high risk for the patient. In recent times a minimally-invasive therapy method has become established. In this method an ablation catheter is introduced via a vein entry into the atrium. The cardiac conduction pathways causing the problems are then severed with the ablation catheter with electrical energy, for example high frequency radiation. With this minimally-invasive therapy, the pathways causing the problem must be visible to the doctor carrying out the treatment so that they can be struck correctly by the ablation catheter. A mapping catheter is generally employed for this purpose, with which the electrophysiological potentials in the heart are recorded locally-resolved prior to the therapy and displayed on a monitor.

BACKGROUND OF INVENTION

The minimally-invasive diagnosis and therapy of tachycardial arrhythmias is carried out in an electrophysiological laboratory in which an angiographic x-ray device, a device for recording an intracardial ECG (iECG), a mapping catheter and also the ablation catheter are available. The method itself is generally known in electroophysiology as radio-frequency ablation or RF ablation. The method for measuring the electrophysiological potentials in the heart for determination of the correct ablation location with the mapping catheter in each case is referred to as mapping.

A method and a device are known from U.S. Pat. No. 6,556,695 B1 for supporting diagnosis and RF ablation as well as mapping, providing the user with better navigation during the actual ablation procedure. In the method 3D images of the heart are created before the beginning of the procedure using a 3D imaging modality, especially a computer tomograph or a magnetic resonance tomograph. These 3D images are registered with the coordinate system of the mapping catheter, so that the 3D images can be shown overlaid together with the mapping data. While the procedure is being carried out 2D images are additionally recorded with an intracardial ultrasound catheter which are also overlaid onto the displayed image data, to give the medical user updated information for orientation and navigation during the procedure. The application of this technology however requires 3D images to be recorded in another station before the procedure, since a computer tomograph or a magnetic resonance tomograph are generally not available in an electrophysiological laboratory. This means a greater outlay in time for patient and hospital staff.

A further problem in carrying out and monitoring minimally-invasive interventions lies in the fact that, when an x-ray device is used as an imaging system, only a restricted access to the patient is possible. The most unrestricted access possible is however precisely what is required with minimally-invasive interventions within the framework of an electrophysiological therapy.

SUMMARY OF INVENTION

An object of the present invention thus consists of specifying a system for carrying out and monitoring minimally-invasive interventions, especially for treatment of electrophysiological diseases, which offers improved access to the patient.

The object is achieved by the system as claimed in an independent claim. Advantageous embodiments of the system are the subject matter of the subclaims or can be found in the description below as well as in the exemplary embodiment.

The present system comprises an x-ray device in which at least one x-ray emitter and an x-ray detector are attached to one or more robotic arms of one or more multi-axis articulated-arm robots with which they are able to be moved for recording images from different projection directions on a predetermined path around a patient support facility. Furthermore the system includes a control and evaluation unit with interfaces for catheters and devices for carrying out the minimally-invasive intervention. The control and evaluation unit is embodied for processing measurement and/or image data which it receives from the catheters and devices and for control of the catheter and devices for detecting the measurement and/or image data. Preferably the control and evaluation unit features a data bus for this via which the interfaces can exchange data with the modules of the control and evaluation unit. Furthermore a user interface for central operation of all catheters and devices as well as a display unit with one or more screens for a central display of the measurement and/or image data recorded by the catheters and devices or derived from said devices are provided.

The proposed system, when the corresponding catheters and devices are used, typically enables tachycardial arrhythmias to be treated without greatly restricting access to the patient by the x-ray device. The imaging components of the x-ray device, i.e. the one or more x-ray tubes and one or more x-ray detectors, can be moved with complete flexibility around the patient in the proposed system. This is achieved by using one or more multi-axis articulated-arm robots, to the robot arms of which the x-ray tubes(s) and the x-ray detector (s) are attached. These types of multi-axis articulated-arm robots allow x-ray tubes and x-ray detectors to move on any given path, preferably circular, elliptical or spiral, around the patient, in order to create projection images from different projection directions in each case. 3D images including 3D soft tissue images can then be reconstructed from these projection images. In addition the times at which the images were created are preferably registered, so that a 4D presentation (with the time as the fourth dimension) can be reconstructed from this. The system thus allows better access to the patient, enables significantly more flexible and also new procedures to be carried out and offers an arrangement of additional tools and devices around the patient better tailored to the medical workflow.

The movement of x-ray tubes and x-ray detector is controlled via the control and evaluation device, which accordingly controls one or more multi-axis articulated-arm robots. For the different projection images the x-ray source can be positioned both below the patient support facility and also above the patient support facility. X-ray tube and x-ray detector can in such cases be attached to the same arm of a multi-axis articulated-arm robot or to separate robot arms of two multi-axis articulated-arm robots.

In an advantageous embodiment the multi-axis articulated-arm robot or robots is or are supported on mobile carriers so that they can, for example using rollers, wheels or chain drives, be flexibly positioned or moved in the room. The movement in the room can also be supported by motorized drives. Naturally the multi-axis articulated-arm robots can also be permanently mounted at one point on the ceiling, the wall or the floor in the room.

X-ray tube and x-ray detector can be attached to the robot arm in different ways. In an advantageous embodiment x-ray tube and x-ray detector are attached to a C-arm opposite one another in the known way, with the C-arm being supported by the robot arm of the multi-axis articulated-arm robot. In this way x-ray tube and x-ray detector can move on movement paths that can also be produced with a conventional C-arm x-ray device. As well as a C-arm, similarly structure supports can naturally also be used on which x-ray tube and x-ray detector lie opposite one another. Examples of such supports are U-shaped or a V-shaped bracket, which are then in their turn supported by the robot arm.

The patient support facility, on which the patient is supported during the intervention, has a support surface transparent to x-rays. The support surface can preferably be adjusted vertically and well as horizontally and transversely either manually or by a motor. Furthermore a tilt or swivel facility can optionally be provided in the x-y-z direction. In a further embodiment the support surface can be rotated around a center point or be embodied to execute circular or elliptical rotational movements around a fixed point in the plane or in the room. The patient support facility can in this case be permanently attached to the floor or likewise supported by a robot arm of a further multi-axis articulated-arm robot.

The control and evaluation unit preferably includes a collision monitoring unit which warns about a collision between components of the x-ray device with the patient support facility and a patient supported thereon and/or prevents such a collision. For this collision monitoring all the relevant dimensions and movement paths on which the components of the x-ray device and the patient support facility or its support surface with the patient respectively are to be moved are known to the control and evaluation unit. The collision monitoring unit then gives a warning of a possible collision before the respective movement is carried out, by generating an alarm for example, and suppresses further movement if a limit range is exceeded.

In an advantageous embodiment an operating unit is provided on or in the immediate vicinity of the patient support facility, via which actions such as a power-assisted manual guidance of the one or more robot arms are made possible. Preferably sensors are integrated into the one or more robot arms for this purpose, via which a force effect during the manual guidance of the robot arm can be detected. After a defined limit value has been exceeded for the force effect the power assistance for guiding the robot arm is switched on or the motorized power assistance already being provided is increased. Naturally this assistance can also be undertaken autonomously without the control unit.

The control and evaluation unit is also preferably embodied such that a user can use the control unit to select an examination program, for example for ablation of pathways with an ablation catheter. After the selection of the examination program all system components, the image processing and the associated emitter, detector position and position of the support surface are then set by the control and evaluation device and automatically moved to said positions. In such cases the collision unit can monitor possible critical positions and create a corresponding alarm or prevent the movement if this would have led to a collision.

In an advantageous embodiment for the treatment of electrophysiological diseases the proposed system also contains at least one ECG recording device, an imaging catheter, a mapping device with a mapping catheter and an ablation device with an ablation catheter, for which corresponding interfaces to the control and evaluation device are provided.

With such a system all necessary steps for a treatment of tachycardial arrythmias can be carried out in an electrophysiological laboratory without further imaging aids. This allows all tachycardial arrythmias to be reliably rectified, with low risk for the patient and the clinical personnel, with high quality and with good therapeutic success. The system is thus not reliant on prior images from computer tomographs or magnetic resonance tomographs. Instead 3D-image data can be created in real time with the present system and for example be overlaid with 2D images or also 3D images, which for example are obtained via a 2D ultrasound catheter with additional location information via a position sensor or also via an ultrasound catheter with an actuator, as is described below. The 3D images are recorded in the present system with the x-ray device embodied for this purpose, with which a 3D-image dataset can be reconstructed from different adjustable projections. The techniques for reconstruction of a 3D image dataset from images taken from different projection directions are basically known.

The control and evaluation unit should in this case feature the corresponding module for the reconstruction of a 3D image dataset from the image data obtained with the x-ray device. Furthermore the control and evaluation unit should also feature a correction module for correction of the image data, which enables soft tissue, especially soft tissue that has moved, to be displayed. The correction to be performed in this case can be selected from the group of truncation correction, x-ray scatter correction, overradiation correction, ring artefact correction, correction of the beam hardening and of the low-frequency drop, as is known for example from DE 10 2004 057 308 A1. A separate correction process for making these corrections can also be provided in the control and evaluation device.

A further significant advantage of the present system lies in the option for exchange of data between all connected devices. The operator in this case does not have to transmit any data or information from a device to the other device in each case, or enter data at this device. Instead it is ensured at all times via the central control and evaluation unit, that all connected devices have available at all times the data necessary for their use or for the use of the other devices. In particular the present system can be operated in the preferred embodiment via a central operator interface or control unit which provides all the necessary information and data. In this embodiment at least one central screen unit with one or more screens or display surfaces (e.g. a large screen with a number of sections) is provided, at which all the data created by the different devices or catheters can be displayed, overlaid if necessary.

Even if the present system for carrying out and monitoring a minimally-invasive intervention does not need any 3D-image data of a computer tomograph or of a magnetic resonance tomograph recorded in advance, in one embodiment of the present systems the option can still be provided for storing such 3D image data in the system and of displaying it with the system, where necessary overlaid by other image or measurement data. In this case a corresponding interface for supplying this type of 3D-image data, for example in the form of a DICOM interface is provided. Furthermore the control and evaluation device then includes a corresponding module for registration of that 3D-image data with the coordinate system or of a number of devices or catheters of the present system as well as for overlaid image display of the external 3D-image data with image or measurement data of the catheters or devices. The external 3D-image data can in this case also be updated with current image data of the x-ray device or of the imaging catheter.

Even if the present invention is primary explained with reference to the application for examination and therapy in heart chambers, especially for treatment of tachycardial arrythmias, it is evident that, in accordance with the inventive system, it can also be used for other vascular vessel examinations and organ examinations, including their minimally-invasive therapies.

BRIEF DESCRIPTION OF THE DRAWINGS

The present system is explained again in more detail below with reference to an exemplary embodiment in connection with the enclosed figures. The drawings show FIG. 1 an example for the arrangement of a number of system components.

DETAILED DESCRIPTION OF INVENTION

Figure 1:
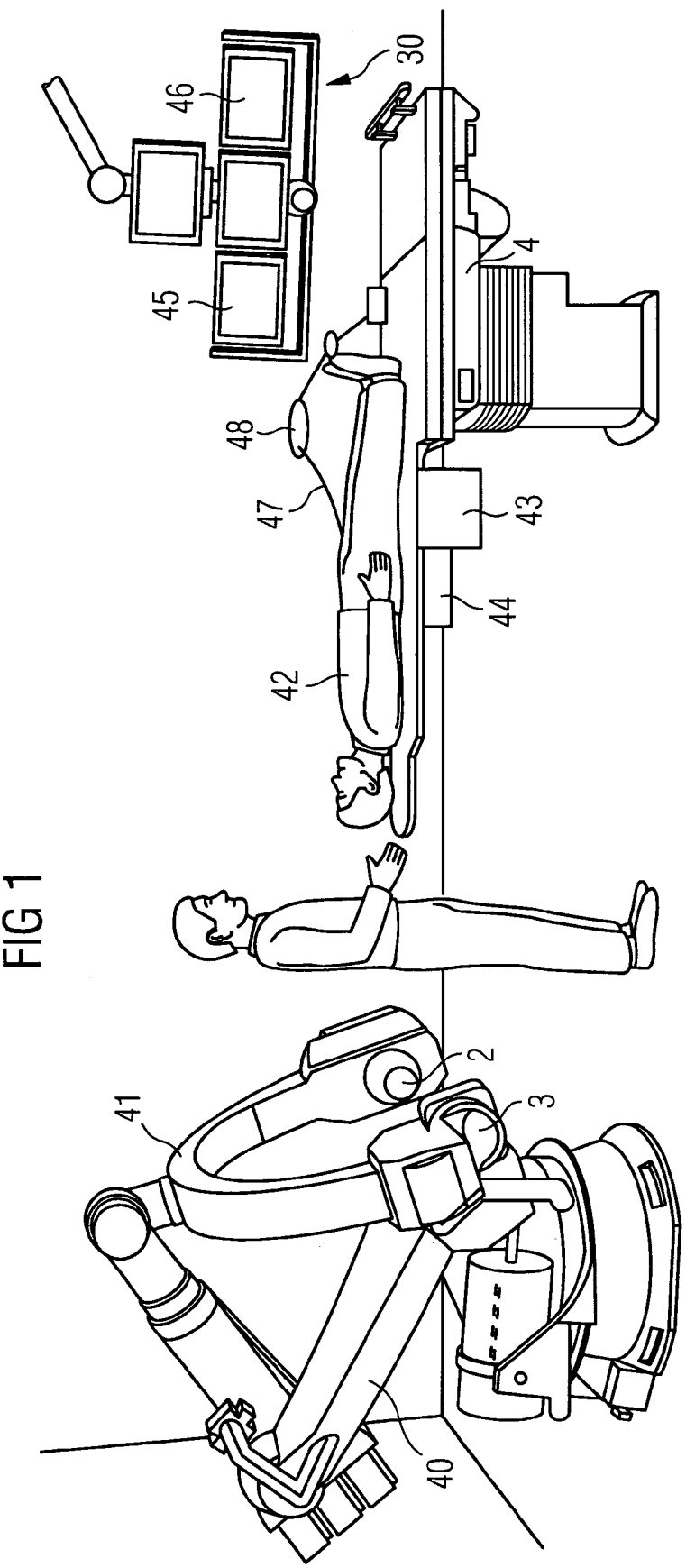

FIG. 1 shows an example for a robot-based integrated electrophysiological laboratory. In this example the articulated-arm robot 40 of the x-ray device is clearly visible, which is mounted on the floor and carries a C-arm 41 with x-ray emitter 2 and x-ray detector 3. The patient support facility 4 with the patient 42 features a control unit 43 close to the patient for the x-ray device and the catheter employed. Connected to this operating unit 43 is an interface unit 44 for connection of different catheters which has a "plug&play" functionality. The operating unit 43 provides the user with selection options, so-called organ or examination programs. If an examination program, e.g. ablation, is selected by the operator, all system components, the image processing and the associated emitter, detector and table positions are set by the system control and the devices are moved automatically to these positions. The images generated by the digital image system for the fluoroscopy recordings, which are contained in the control and evaluation device, are displayed on the screen or display unit 30, which in this example includes 6 LCD displays. One of the displays 45 is intended for the catheter imaging, a further display 46 for the display of fused images. FIG. 1 shows a catheter 47 with a so-called "Robotic Catheter Manipulator" 48 via which the user is able to undertake the mechanical navigation of the catheter. The control and evaluation device is not identifiable in this diagram. It is however connected to the individual components of the system shown.

Figure 2:
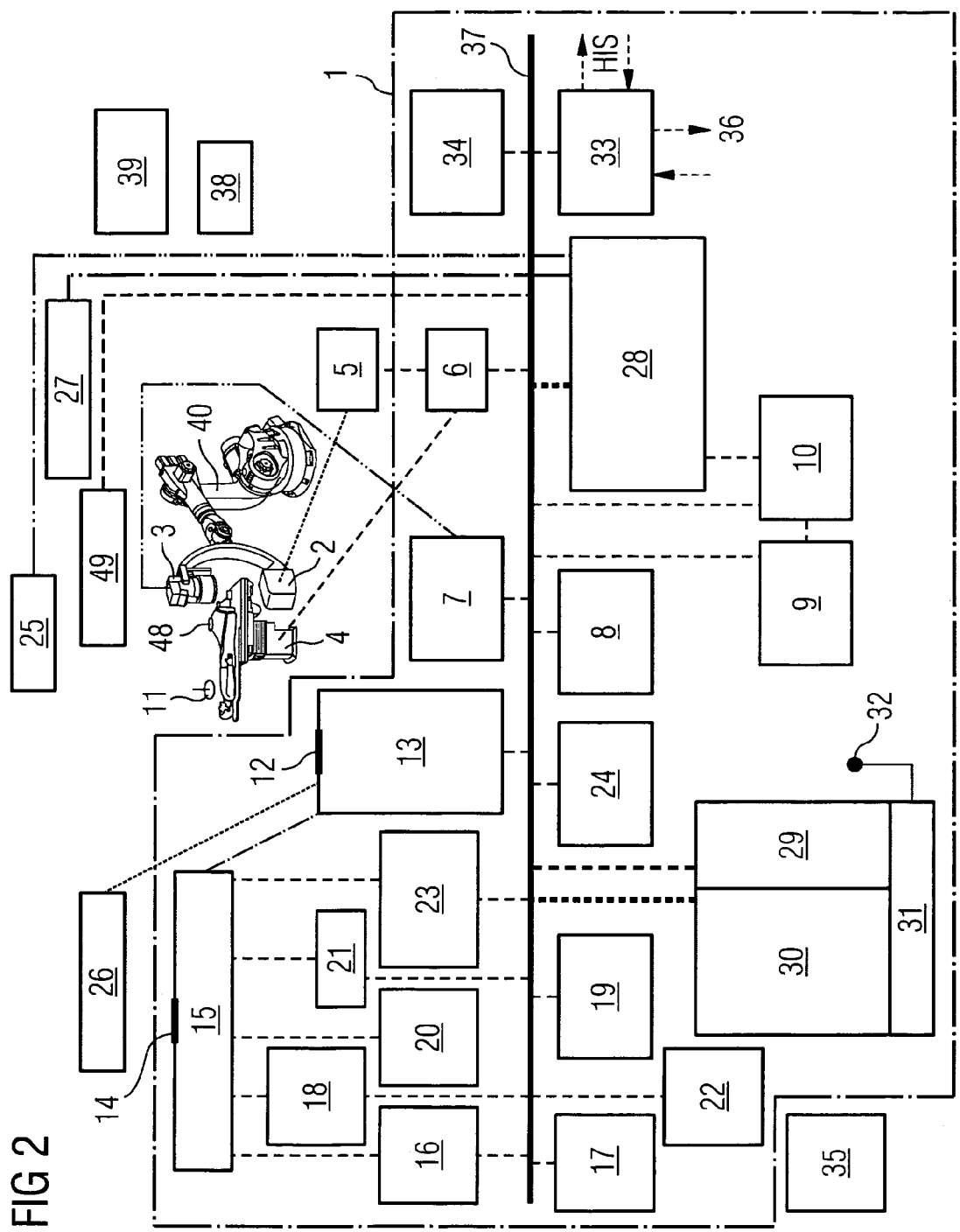
FIG. 2 a schematic diagram of the system in an embodiment containing numerous optional components.

The area in FIG. 2 depicted by a dashed outline indicates in this case the control and evaluation unit 1 with the associated modules. Of course individual of these modules can be embodied as part of the individual devices, especially if these modules carry out preprocessing of the detected measurement or image data which is generally required for these types of devices or catheters.

The system shown by way of example in the figure comprises an x-ray device for cardiological examination, which in this example is a 6-axis articulated-arm robot 40 and a C-arm attached to the robot arm of the articulated-arm robot with an x-ray emitter 2, a diaphragm as well as an x-ray detector 3, for example with a flat-panel detector or aSi detector. A holder device for the C-arm is mounted on the robot arm for this purpose. The patient support table 4 can have a plate transparent to x-rays for patient support. In the preferred embodiment this patient support table 4 makes possible a longitudinal tilting as well as a sideways tilting with a tilt capability of up to 90°, with all movements of the patient support table being able to be undertaken with power assistance. The x-ray emitter or emitters 2 are connected to a high-voltage generator 5. The x-ray image recording is controlled via the system control 6, which in the present example is embodied as a module of the control and evaluation unit 1. For a 3D image to be recorded the C-arm is moved with the robot arm by at least an angle of 180° and records a rapid sequence of projection images during this process. The raw data recorded in this case is initially preprocessed in a preprocessing module 7. A 3D image is reconstructed in the image processing module 8 for x-ray images. The two modules 7, 8 are in each case a component in the present example of the control and evaluation unit 1. Reference symbol 35 indicates the power supply unit of the system.

The 3D recorded images can be additionally supported by administering contrast media. Because of the movement of the heart an ECG control is required, to enable the 3D reconstruction to be carried on the 2D image data in the same heart phase. The ECG device is not explicitly shown in the figure. The control and evaluation unit 1 however features a corresponding terminal 12 for physiological sensors to which the ECG device is connected. The ECG data is processed in the associated signal processing module 13 for physiological signal processing. This module 13 also processes further signals, such as an ECG signal as well as other physiological signals, preferably for blood pressure, the breathing and the body temperature.

The physiological measuring device, which is connected to the corresponding terminal 12, can also include components for non-invasive blood pressure measurement (NIBP), for a partial oxygen measurement (SpO2) and for a cardiac output measurement, especially a non-invasive cardiac output measurement. A suitable measuring device is offered for example by Osypka Medical GmbH under the product name Aesculon®.

The recorded data, which is received via the terminal 12, can be displayed with image information of the other devices together on a screen or overlaid. Methods for reconstruction of 3D images of a moving heart are known to the person skilled in the art for example from US 2002/0181645 A1 or 2005/0058248 A1.

As well as the last-mentioned method the 3D images can also be created with images of discrete tomography from just a few projections, especially since a first 3D-image dataset has been created at high resolution. A method for discrete tomography is for example described in US 2004/0008882 A1. This type of recording technique has the advantage that the patient and the clinical staff are only subjected to a small exposure to radiation as a result of the smaller number of required projections.

In addition a 2D-3D fusion can be applied during the procedure. To this end 3D images of the heart and/or lung veins are created at high quality, preferably by the x-ray device. The 3D images serve as basic image material. With the therapy it is especially important to make the feed tubes and the mouth of the lung veins visible. To make the lung vein easily visible a contrast medium can preferably be injected into the lung veins and a normal 3D angiography of the lung veins displayed. The heart chambers can thereafter be created once again as 3D soft tissue displays by an x-ray device. In the further progress of the therapy these 3D basic images are updated with fluoroscopic 2D images, which are likewise recorded with the x-ray device. Alternatively MR or CT preliminary images can also be overlaid with fluoroscopic 2D images in real time. This has the advantage that patient and medical personnel are subjected to a lower radiation dose and the image reconstruction times can be reduced.

In the present example the control and evaluation unit 1 includes an image correction module 10, preferably with a special processor unit, for rectification of movement artefacts which are caused by patient movement and/or breathing. To remedy the breathing artefacts at least one sensor 11 is provided for patient movement, which can for example be integrated in a breast band for the patient. The one or more sensors 11 in this breast band supply data for breath amplitude and -frequency, which are used in the image correction module 10 for correction calculations which calculate the movement artefacts from the image information of the x-ray device. Preferably a calibration module 9 is also provided in this case which carries out a calibration of the x-ray recording system, for example a geometry, distortion removal, intensity and/or gain calibration. These types of calibration and image correction techniques with x-ray devices are basically known to the person skilled in the art. As well as the data of the sensor 11 the amplitude and frequency of the breathing is also calculated from the height curve of the ECG signal and fed to the image correction module 10. With this type of image correction, and where necessary calibration the display of soft tissue is enabled in the 2D or 3D x-ray images.

Furthermore an auxiliary position sensor (e.g. with electromagnetic operating principle) can be used to detect movements of the patient on the patient support table 4. To make the fewest possible cable connections to the patient and to obtain a largely unimpeded access to the patient, this auxiliary sensor is preferably embodied as a wireless sensor, for example with a Bluetooth transmitter. Alternatively the position of the patient can also be detected by an optical camera and patient movements or displacements can be corrected with computational methods of pattern recognition in the respective image processing module. As an additional option the patient can be scanned with a laser beam in order to determine and correct position displacements.

The proposed system preferably also comprises a device for ultrasound examination with at least one ultrasound catheter, for example a so-called AcuNav catheter. For imaging catheters one or more connections 14 to the control and evaluation unit 1 are provided, which is connected to a corresponding interface 15. This interface 15 is embodied in the present example for AcuNav catheters and IVUS catheters (IVUS=Intravascular ultrasound), for IntraMR catheter (IntraMR=Intracorporal or Intarvascular Magnet Resonance), for OCT-catheters (OCT=Optical Coherence Tomography) or also for optical endoscopes as well as for position sensors. Accordingly the control and evaluation unit 1 in the present example also features preprocessing module 16 as well as an image processing module 17 for OCT, a preprocessing module 18 for AcuNav, a preprocessing module 20 for IVUS, an image processing module 19 for AcuNav and IVUS, a preprocessing module 21 as well as an image processing module 22 for IntraMR, a preprocessing module 23 as well as an image processing module 24 for the position sensors. Basically not all an image processing modules for image catheters have to be present in the system. Instead at least one processing module is sufficient.

When the ultrasound catheter is used an ultrasound contrast medium can be used in addition to improve the ultrasound imaging, especially the 3D imaging. The ultrasound catheter is in this case preferably provided with an actuator which allows a three-dimensional ultrasound detection almost in real time. The actuator turns the ultrasound catheter or its detection head in this case by a specific angle, in order to record 2D cross-sectional images which can be combined into a 3D image. Alternatively the detection head of the catheter can also contain a three-dimensional array instead of a two-dimensional array of send and receive units.

In addition the ultrasound catheter can be provided with a lumen with a diameter of appr. 0.5 to 2 mm through which a corresponding OCT catheter (OCT: Optical Coherence Tomography) can be guided into the vessels of the heart chambers in order to observe at high resolution the ablated tissue locations at close hand. Suitable OCT catheters are for example known from 00/43730 A1 or 01/11409 A2. In such cases the OCT catheter can be additionally provided with magnets in order to be guided by an external magnetic field into the corresponding position. An example of this is known from DE 102 55 957 A1. As an alternative to the magnets, mechanical control facilities can be used with these catheters as with all other catheters, making it possible to turn and to bend the catheter by tensile and compression effects. In such cases specific sections of the catheter, preferably the tip of the catheter are explicitly bent using a pulling device which is inserted into the corresponding catheter, to move it into the corresponding position. A device of this type with a "Robotic Catheter Manipulator" 48 for mechanical activation of catheters is for example offered by Hansen Medical, Inc.

In addition the OCT catheter can be provided with position sensors which use external position sensors to enable the spatial position of the catheter to be located and thereby to generate 3D OCT images. To this end methods can be used which are known for reconstruction of 3D ultrasound images from 2D ultrasound images.

The ultrasound catheter can additionally be provided with a magnet to enable it to be better controlled. An example of this can be found in U.S. Pat. No. 6,772,001 B2. As an alternative to the magnet, mechanical control facilities can be used here too to make it possible to turn and to bend the catheter by tensile and compression effects. The ultrasound catheter too can be provided with position sensors which use external position sensors to enable the spatial position of the catheter to be located and thereby the generation of 3D ultrasound images. Methods for this are known for example from US 2003/0220561 A1 or US 2003/0199748 A1.

In addition to or as an alternative to the lumen already mentioned the ultrasound catheter can be provided with a further lumen with a diameter of appr. 0.5 to 3 mm, through which the corresponding IVUS catheter (IVUS: Intravascular Ultrasound) can be routed into the vessels of the heart chamber in order to observe the ablated tissue locations with good resolution at close hand. An IVUS catheter is described for example in EP 0 885 594 B1. The IVUS catheter can here too be additionally provided with magnets in order to be guided by an external magnetic field into the corresponding position. As an alternative to the magnet, mechanical control facilities can be used here too to make it possible to turn and to bend the catheter in the space by tensile and compression effects. In addition the IVUS catheter can be provided with position sensors which use external position sensors to enable the spatial position of the catheter to be located and thereby to generate 3D IVUS images.

As an alternative to the intracorporal ultrasound catheter explained an intracorporal MR catheter or a intravascular MR catheter can also be used which delivers high-resolution images of the vessels, heart chambers and medical instruments. These catheters too can be additionally provided with magnets to enable them to be guided by an external magnetic field into the corresponding position. As an alternative to the magnet, mechanical control facilities can be used here too to make it possible to turn and to bend the catheter by tensile and compression effects. These catheters too can be provided with position sensors which use external position sensors to enable the position of the catheter to be located and thereby 3D images to be generated. The methods already mentioned can be used for this purpose, which are also used for 3D image generation with ultrasound.

The present system also includes a device for measuring and recording the electrical activities in the heart, especially intracardial ECG (iECG), referred to below as a mapping device 25. An example of such a mapping device 25 with mapping catheter can be found in U.S. Pat. No. 6,738,673 B2. In this case mapping catheters can be used which are in direct contact with the epicard and/or mapping catheters which are not in direct contact with the endocard. The mapping catheter of the mapping device 25 can additionally be provided with magnets, permanent or electromagnets, to enable it to be controlled via an external magnetic field. As an alternative to the magnet, mechanical control facilities can be used to make it possible to turn and to bend the catheter in the space by tensile and compression effects. In addition the mapping catheter can be provided with position sensors which use external position sensors to enable the spatial position of the catheter to located and allow 3D potential field images to be generated. Known methods can be used for this, for example electro-anatomical mapping, as implemented in the CARTO® system from Biosense-Webster. Furthermore contactless mapping with the aid of a balloon catheter can be used, in which with the aid of mathematical model the potential distribution on the endocard of the heart is calculated. A further option consists of the method for calculating positions of electrodes on catheters with the aid of impressed currents, as implemented in the systems Localisa® from Medtronic and Navex® from Endocardial Solutions. A system for location by means of ultrasound sensors accommodated on the catheter, as implemented in the RPM® system (Realtime Position Management) from the Boston Scientific Corporation can also be used in this case.

The present system also includes an ablation device 26 for ablation of the undesired pathways with the aid of an ablation catheter. A device of this type is known for example from U.S. Pat. No. 5,409,000 A1. The ablation catheter can in this case additionally be provided with magnets (permanent magnets or electromagnets). As an alternative to the magnet, mechanical control facilities can be used to make it possible to turn and to bend the catheter in the space by tensile and compression effects. In addition the ablation catheter can be provided with position sensors which use external position sensors to enable the position of the catheter to be located and thereby relative to the 3D potential images which were recorded with the mapping catheter. Electrical and magnetic alternating fields, ultrasound, laser beams, heat or cold probes can be used to generate the ablation energy. Severing of the pathways by delivery of clinical, pharmaceutical and/or biological agents with suitable ablation catheters is also possible.

The present system preferably also comprises a subsystem for position detection of one or more of the catheters and medical instruments, which are provided with corresponding position sensors. This option has already been alluded to in the description of the individual catheters. Different options are available for this position detection. A preferred option is electromagnetic position determination, for example using the MPS (Magnetic position system) from Mediguide, as is described in US 2002/0049375 A1. In addition to the solution described there it is proposed that the image information of the MPS be combined with or overlaid with the medical images described above, preferably the 3D images. In the known manner this demands the calibration and registration of the different subsystems for the subsequent image fusion. For calibration the tip of the guide wire of the catheter is recorded at least once by at least two x-ray projections in the space (x, y, z) and the position in space is determined at least once by the electromagnetic location system (x', y', z'). With a transformation the two positions are subsequently calibrated to each other. It is of advantage in this case for the calibration only to be carried out after installation in the electrophysiological laboratory. The accuracy of the calibration can be increased by the use of a body phantom and a calibration with a number of points.

The image diffusion module 28 allows the positions and images determined with the position sensor to be overlaid in 2D, 3D and 4D with images which have been created with the following techniques: Sonography, including IVUS and AcuNav method, radiography, fluoroscopy, angiography, Optical Coherence Tomography (OCT), discrete tomography, Positron Emission Tomography (PET), Single Photon Emission Computed Tomography (SPECT), other nuclear medical diagnostics, computer tomography, nuclear resonance tomography, including catheter MR, optical imaging including endoscopy, fluorescence and optical markers (molecular Imaging).

The coils required for electromagnetic position determination in the position sensor on the catheter or medical instrument are preferably not exclusively arranged orthogonally to each other, but at any given angle of for example 60°, in order to achieve a better miniaturization. This miniaturization enables the position sensors to be better integrated into a catheter. The deviation of the orthogonal arrangement can be corrected for the position sensors by appropriate computation algorithms in the image processing module 24. To improve the miniaturization only one electric conductor is routed back to the signal connections for each sensor coil. The conductive guiding wire of the catheter as well as the human body with its blood vessels is used as a neutral electrode. In addition a signal multiplexer can be integrated into the tip of the guide wire which cyclically interrogates the receive antennas. This leads to a further reduction in the signal lines required. In addition the send coils can also be operated and evaluated cyclically, in specific time segments, with different frequencies, to increase the accuracy of the location finding. The electromagnetic position sensors can be designed in this case so that, by using iron cores for example, these can also serve by corresponding activation optionally as electromagnets for control of the respective catheter with an external magnetic field.

Preferably the subsystem for position detection also includes a calibration unit, which stores the static and dynamic magnetic fields in the different functional stages, for example through movements of the C-arm of the x-ray device, and takes them into account in the signal evaluation and correction calculation for the image editing. The individual components of the subsystem for position detection, especially functional units and signal lines, are equipped with facilities which shield the physiological signals and image signals as well as the signal processing and editing against the magnetic fields of the send antennas. One of the solutions can be to encapsulate the components with a conductive metal sheath, made of copper for example. Another option is coating with thin film layer made of conductive nanoparticles (e.g. nanoparticles of silicon dioxide, aluminum oxide, silicon nitrate, carbon). Initial attempts at magnetic shielding have been made by Biophan (cf. http://www.biophan.com/shielding.php). Magnetic shielding with nanoparticles is known from U.S. Pat. No. 6,506,972 B1. The miniaturization of the position sensors can be increased additionally by use of nanotechnology during their manufacture.

As well as electromagnetic position determination other techniques of position determination are also possible, for example by means of ultrasound, as is described for example in U.S. Pat. No. 6,038,468 A.

A corresponding subsystem can be provided for magnetic navigation of the catheter comprising corresponding magnets, mechanical holders, control electronics and operating units of the navigation system, with the operating units in their turn being implemented in the control and evaluation unit 1. An example of a subsystem of this type is known from U.S. Pat. No. 6,148,823 A. Such a subsystem is however only present as an option in the inventive system, as is a 3D color doppler unit 27, which, with an ultrasound sampling head arranged outside the chest of the patient, can supply additional picture information if required. These recorded images can be overlaid with the other 2D, 3D and 4D images obtained by the x-ray device or the catheter. The image fusion module 28 required for this is a major component of the present control and evaluation unit 1. This image fusion module 28 is used for segmentation, auto segmentation, registration, image reconstruction and image overlaying of the different measurement and image data received by the various individual components of the present system. Suitable techniques for registration, image segmentation and image overlaying, especially 2D-2D, 2D-3D, 3D-3D, 2D-4D and 3D-4D are known to the person skilled in the art. These types of overlays offer diagnostic benefits not previously available. Examples of such image fusions are known from DE 102 10 645 A1, DE 102 10 646 A1 or U.S. Pat. No. 5,706,416 A1.

The present system in this case also enables the intracardial electrical activities recorded with the mapping catheter to be overlaid with the medical, especially anatomical, images of the heart. The registration or overlaying of the image data of the patient with the position data of the catheter requires the spatial coordinates of the two objects to be transferred into a common coordinate system. The movements of the patient on the examination table can in this case for example be determined with the auxiliary position sensor already mentioned above.

The control and evaluation unit 1, which forms the digital image system, is preferably constructed as a integrated processing unit with processor(s), memory (memories) and one or more screens, but can also be formed by a number of distributed processing units (workstations). A major feature however is that the system can be operated with a central user interface 29 (user input/output unit or operating unit 43) with an associated display unit 30. All inputs and control commands for the system can be entered for the system via the user interface 29. Displayed on the display unit 30, which can also consist of a number of screens arranged alongside one another, are the generated medical images, preferably AcuNav/OCT/IVUS-/IntraMR-/position sensor and x-ray images, if necessary shown in an appropriately overlaid display. The optional CT or MR images also stored in the system which must be created before the procedure, are also displayed on this display unit 30. This means that the information about the corresponding images is visible at one location for the user and thus makes possible a faster and better diagnosis.

The display unit 30 can include an appropriate display for presentation of 3D images, preferably in the form of a flat-screen display, as is known for example from the Technology Report CT IRC TIS from Siemens, "Autostereoskopische 3D-Displays und "Verfahren" (Autostereoscopic 3D Displays and -Methods) October 2003, by Ulrich Walter and Dr. Eckart Hundt. This solution allows three-dimensional viewing without aids such as 3D eyeglasses for example. A suitable 3D display control 31 is necessary for this. In addition the viewer can wear a headband or normal eyeglasses with position sensors, so that the direction of view of the observer can be synchronized via corresponding processors with the viewing of the 3D object shown on the screen. One example for determining the direction of view of an observer when following an image object can be found for example in U.S. Pat. No. 5,646,525 A. An appropriate receiver 32 for receiving data, from which a head movement of the observer can be determined must be provided for this at the 3D display controller 31.

The operating units of the x-ray device, of the AcuNav/OCT/IVUS devices, of the magnetic navigation system, of the electrophysiological mapping device as well as of the ablation device are combined or connected together in an integrated solution in accordance with the medical workflow. In the present system recording of preliminary images by CT or MR can be dispensed with. In addition to already known solutions it is possible with the present system to create 3D-image data in real time and overlay it with 2D images. By using an MPS subsystem the use of contrast means and the applied x-ray dose can be reduced. This embodiment has the further advantage that, in addition to angiographic x-ray methods good images of the heart wall can be obtained by 3D ultrasound imaging and thus the state before and after an ablation can be shown. The present system is not restricted to the treatment of tachycardial arrythmias but a variation thereof can also be employed for minimally-invasive interventions of any type in the heart and in other organs, for example for heart valve repair.

The present system preferably contains a DICOM interface 33 for the exchange of patient data and image data with a Hospital Information system (HIS) as well as an interface 36 for receiving images of other modalities (e.g. CT, MR, PET, SPECT). Furthermore an image data memory 34 is provided for storing the processed image data. The corresponding power supply unit 35 for the system is also indicated in the figure.

A major feature of the present system lies in the fact that all measurement, control and if necessary patient data can be exchanged between the individual modules or components of the system via a common data bus 37. In this way the data provided by the different components and modules is available at any time at the other locations at which it is needed.

The connections for the physiological sensors and the catheter are preferably decoupled via a corresponding electrical isolation from any ac mains voltage, in order not to endanger the patient. An optical decoupling is especially advantageous here. In an advantageous embodiment of the system all subsystems can be designed to be magnetically compatible, so that they operate without problems in the vicinity of a magnetic navigation system.

The 3D images are preferably displayed by the display unit 30 using standard hardware from the PC/video/game industry, for example using 3D graphics cards or chips from ATI or Nividia. This represents a cost-effective solution for 3D presentation, volume rendering and shading.

To expand the present system it is proposed to attach a temperature sensor to the tip of at least one of the catheters used for the procedure, preferably to the tip of the ablation catheter which registers the temperature in the area of the ablation point. Conclusions about a successful ablation can then be drawn from this temperature.

In addition it is proposed that a pressure sensor be attached to the tip at least one catheter used for the procedure, which records the pressure in the heart chamber in the area of the ablation point. This also allows conclusions to be drawn about the procedure, for example about a short-term increase in the vaporization or ablation of tissue. A suitable miniature pressure sensor which is integrated into the guide wire is for example known from US 2003/0040674 A1. Alternatively the normal blood pressure in the heart chamber can also be recorded, so that the introduction of a separate blood pressure catheter can be avoided.

As a further expansion of the present system a subsystem for application of a narcotic is proposed, for example a narcotic ventilator 38, as is commercially available. In addition a defibrillator or heart pacemaker 39 can be provided for defibrillation and heart pacemaker stimulation for cardiological emergencies.

As an additional expansion the system can also include a hemodynamics measurement system which allows a standardized evaluation of the pressure and temperature measurements. One example of this is the Sensis® or Cathcor® system from Siemens.

Further additional subsystems which can be used as part of the present system, are a patient monitoring system for monitoring the vital functions of a patient or a contrast medium injector, for making it possible to display hollow structures in the heart and vessels. With the patient monitoring system for example an alarm can be triggered, if specific limits of the vital parameters of a patient are overshot or undershot.

Furthermore the system can also include a 2D ultrasound device 49, to enable the introduction of the puncturing needles for the Seldinger technique to be better monitored.

Illustrated below are three typical procedures for use in the system shown as an example. The first example executes the following main steps:

Before the actual procedure:
Inclusion of the demographic data of the patient in the hospital information system,
Transmission of the patient information to a high-resolution 3D-examination unit (CT, MR),
Recording and reconstruction of the high-resolution 3D images or datasets
Preferably automatic segmentation of the relevant image area, and
Transmission of the patient information and high-resolution 3D datasets to the present system.
During the procedure:
Calibration of the ultrasound catheter with position sensors and registration with the available high-resolution 3D images,
Introduction of the ultrasound catheter under x-ray control and/or with the aid of the positioning system,
Update (segmentation, registration, fusion) in the target area of the available high-resolution 3D image with current 3D ultrasound data,
Introduction of the mapping catheter and recording of the intracardial ECGs under x-ray control and/or with the aid of the positioning system,
Update (segmentation, registration, fusion) in the target area of the available high-resolution 3D image with current 3D ultrasound data,
Overlaying of the mapping images with the anatomical image of the heart chambers,
Introduction of the ablation catheter under x-ray control and/or with the aid of the positioning system,
Update (segmentation, registration, fusion) in the target area of the available high-resolution 3D image with current 3D ultrasound data,
Ablation of the selected tissue locations,
Checking the ablation by OCT catheter and/or temperature measurement and/or pressure measurement or renewed mapping, or with another method known to the person skilled in the art,
Removing all medical instruments and aids from the target area,
Documentation and archiving of the procedure in the HIS
Discharging the patient,
Creation of the bill and billing by the HIS, for example with support by DICOM-MPPS (Modality Performed Procedure Step),
As an alternative to the ultrasound catheter the procedure can be conducted with an MR catheter, and
As an alternative to the OCT catheter an IVUS catheter or an IVMRI catheter (IVMRI=Intra Vascular Magnetic Resonance Imaging) can be used.

The second example provides for the following main steps which are all executed during the procedure. No procedural steps are required before the actual procedure:
Inclusion of the demographic data of the patient in the hospital information system,
Recording and reconstruction of high-resolution 3D images or datasets with the x-ray device (with the facility for displaying soft tissue, e.g. from Siemens, known as DynaCT®),
Preferably automatic segmentation of the relevant image area
Calibration of the ultrasound catheter with position sensors and registration with the high-resolution 3D images recorded by the x-ray device.
Introduction of the ultrasound catheter under x-ray control and/or with the aid of the position detection system and/or using a location from at least 2 projections in the x-ray image,
Update (segmentation, registration, fusion) in the target area of the available high-resolution 3D image with current 2D and/or 2D ultrasound data,
Introduction of the mapping catheter and recording of the intracardial ECGs under x-ray control and/or with the aid of the positioning system and/or using a location from at least 2 projections in the x-ray image,
Update (segmentation, registration, fusion) in the target area of the available high-resolution 3D image with current 2D and/or 2D ultrasound data,
Overlaying of the mapping images with the anatomical image of the heart chambers,
Introduction of the ablation catheter under x-ray control and/or with the aid of the positioning system and/or using a location from at least 2 projections in the x-ray image, Update (segmentation, registration, fusion) in the target area of the available high-resolution 3D image with current 2D and/or 2D ultrasound data, Ablation of the selected tissue locations, Checking the ablation by OCT catheter and/or temperature measurement and/or pressure measurement or by renewed mapping, or with another method known to the person skilled in the art, Removing all medical instruments and aids from the target area, Documentation and archiving of the procedure in the HIS, Discharging the patient, Creating the bill and billing by the HIS, for example with support by DICOM-MPPS, As an alternative to the ultrasound catheter the procedure can be conducted with an MR catheter As an alternative a new 3D x-ray image can be made from a few projections during the procedure which will be used for an update of the high-resolution 3D x-ray images, and An IVUS catheter or an IVMRI catheter can be used as an alternative to the OCT catheter.

In the third example the following major steps are executed:

Before the actual procedure:
As with the first example
During the procedure:

Recording and reconstruction of the high-resolution 3D images or datasets with the x-ray device and update (segmentation, registration, fusion) of the high-resolution 3D images (CT or MR) created before the procedure by the x-ray images (with the option of displaying soft tissue, e.g. from Siemens known as DynaCT®), Preferably automatic segmentation of the relevant image area Calibration of the ultrasound catheter with position sensors and registration with the available high-resolution 3D images, Introduction of the ultrasound catheter under x-ray control and/or with the aid of the positioning system and/or using a location from at least 2 projections in the x-ray image, Update (segmentation, registration, fusion) in the target area of the available high-resolution 3D image with current 3D ultrasound data, Introduction of the mapping catheter and recording of the intracardial ECG under x-ray control and/or with the aid of the positioning system and/or using a location from at least 2 projections in the x-ray image, Update (segmentation, registration, fusion) in the target area of the available high-resolution 3D image with current 3D ultrasound data, Overlaying of the mapping images with the anatomical image of the heart chambers, Introduction of the ablation catheter under x-ray control and/or with the aid of the positioning system and/or using a location from at least 2 projections in the x-ray image, Update (segmentation, registration, fusion) in the target area of the available high-resolution 3D image with current 3D ultrasound data, Ablation of the selected tissue locations, Checking the ablation by an OCT catheter and/or temperature measurement and/or pressure measurement or renewed mapping or with another method known to the person skilled in the art, Removing all medical instruments and aids from the target area, Documentation and archiving of the procedure in the HIS, Discharging the patient, Creating the bill and billing by the HIS, for example with support by DICOM-MPPS, As an alternative to the ultrasound catheter the procedure can be conducted with an MR catheter As an alternative a new 3D x-ray image can be made from a few projections during the procedure which will be used for an update of the high-resolution 3D x-ray images, and An IVUS catheter or an IVMRI catheter can be used as an alternative to the OCT catheter.

As a result of the minimally-invasive interventions currently used in cardiology three types of advantageous variants of the proposed system can be presented which are each produced by combining a subset of the described subsystems. This allows an advantageous variant to be designed for the electrophysiological laboratory as a combination of the following subsystems or functionalities:

For treatment of heart arrythmias a combination of ablation device, x-ray device (with the facility for displaying soft tissue, e.g. from Siemens, known as DynaCT®), a module for 2D-3D or 3D-3D registration, a module for processing of preoperative 3D-image data recorded, a mapping system, a module for image integration of electro-anatomical data with anatomical data from CT, MR, ultrasound or other anatomical imaging methods, an AcuNav or intracardial ultrasound catheter with 2D or 3D ultrasound device, a module for updating 3D images with 2D images, or 3D images with 3D images or 4D images as well as a subsystem for magnetic navigation or mechanical navigation of catheters.

For interventional cardiology a combination of an OCT catheter, an IVUS catheter, an MPS position determination system, a workstation for 3D reconstruction and presentation of vessels, catheters and tools, an x-ray device preferably C-arm based), a module for tomographic reconstruction of 3D images from a few projections of the x-ray device, a subsystem for magnetic navigation or mechanical navigation of catheters and tools, a device for introduction of stents, catheters and minimally-invasive tools, as well as a contrast agent injector.

For pediatrics, where its is particular important to reduce the exposure to radiation and the amount of contrast agent for the juvenile patient, a combination of a AcuNav catheter, a 3D ultrasound catheter, an OCT catheter, an x-ray device (preferably C-arm based), a module for 2D-3D registration, a subsystem for magnetic navigation or mechanical navigation, an MPS positioning system, a module for processing preoperative MR data as well facilities for repair of heart valves or for example septal defects.

The invention claimed is:

1. A system for carrying out and monitoring a minimally-invasive intervention, comprising:
an x-ray device having an x-ray emitter and an x-ray detector;
a multi-axis articulated-arm robot, wherein the x-ray emitter and the x-ray detector are attached to at least one robotic arm of the multi-axis articulated-arm robot, wherein the x-ray emitter and the x-ray detector are moveable for recording images from different projection directions on a predetermined path around a patient support facility; and a control and evaluation unit with interfaces for a plurality of catheters and devices to be used for the minimally-invasive intervention, wherein the control and evaluation unit processes data selected from the group consisting of measurement data, image data and a combination thereof, wherein the control and evaluation unit receives the data from the catheters and devices, and wherein the control and evaluation unit controls the catheters and devices for the detection of the data, wherein the system has a position determination device connected for an exchange of data to the control and evaluation unit for a determination of a three-dimensional position of one or more of the catheters in the space which are equipped with position sensors for detection of the three-dimensional position, wherein at least one catheter has at least two coils or antennas arranged at an angle to each other as position sensors, and wherein a navigation device is connected for the exchange of data with the control and evaluation unit for a magnetic navigation of one or more of the catheters, wherein the catheters have magnets for magnetic navigation using an external magnetic field generated by the navigation device.

2. The system as claimed in claim 1, wherein the articulated-arm robot is supported on mobile carrier.

3. The system as claimed in claim 1, wherein the patient support facility is inclineable or tilteable within a room.

4. The system as claimed in claim 1, wherein the patient support facility is rotateable on a circular or elliptical path around a fixed point in a room.

5. The system as claimed in claim 1, wherein the patient support facility is attached to a robot arm of a further multi-axis articulated-arm robot.

6. The system as claimed in claim 1, wherein the control and evaluation unit has a collision monitoring unit which warns before a collision of components of the x-ray device with the patient support facility and a patient supported thereon or with the operating personnel, wherein the system further comprises an imaging catheter, a mapping device with a mapping catheter and an ablation device with an ablation catheter, with an interface for a data exchange with the control and evaluation unit, and wherein a control unit provides a power assistance for a manual guidance of at least one robot arm.

7. The system as claimed in claim 6, wherein sensors are integrated into at least one robot arm to detect a force effect for a manual guidance of the robot arm, wherein, if a limit value for the force effect is exceeded, the manual guidance of the robot arm is power-assisted or a power assistance is increased.

8. The system as claimed in one of the claim 1, wherein the control and evaluation unit has an operator interface for central operation of all catheters and devices and a screen unit for a central display of the measurement or image data of the catheters and devices or of data derived from it, wherein a user selects a treatment program via the operator interface and subsequently power-assisted components of the system move based upon the control and evaluation unit to start positions for a selected treatment program.

9. The system as claimed in claim 8, wherein the screen unit has a 3D display for a three-dimensional visualization, and wherein the control and evaluation unit registers and overlays measurement or image data recorded by the catheters.

10. The system as claimed in claim 1, wherein the control and evaluation unit has a module for processing and displaying three-dimensional image datasets as well as optionally data of a 2D ultrasound device, wherein the control and evaluation unit has a module for an activation of x-ray devices for the recording of a 3D image dataset, and wherein the control and evaluation unit has a module for creating a 3D image dataset from image data of different projections of the x-ray device by way of discrete tomography.

11. The system as claimed in claim 1, wherein the catheter is selected from the group consisting of an ultrasound catheter for recording intraluminal sectional images, a MR catheter, an optical endoscope, and a Robotic Catheter Manipulator.

12. The system as claimed in claim 1, further comprising a 3D color doppler device connected for an exchange of data with the control and evaluation unit with an ultrasound scanner head.

13. The system as claimed in claim 1, further comprising a contrast medium injector connected for an exchange of data with the control and evaluation unit, and a physiological measuring device for an exchange of data with the control and evaluation unit which features a module for non-invasive measurement of the blood pressure or a module for partial oxygen measurement or a module for non-invasive cardiac output measurement.

14. A method of treating tachycardial arrhythmias of a heart, comprising:
providing a system for carrying out and monitoring a minimally-invasive intervention,
having:
an x-ray device having an x-ray emitter and an x-ray detector, a multi-axis articulated-arm robot, wherein the x-ray emitter and the x-ray detector are attached to at least one robotic arm of the multi-axis articulated-arm robot, wherein the x-ray emitter and the x-ray detector are moveable for recording images from different projection directions on a predetermined path around a patient support facility, and
a control and evaluation unit with interfaces for catheters and devices to be used for the minimally-invasive intervention, wherein the control and evaluation unit processes data selected from the group consisting of measurement data, image data and a combination thereof, wherein the control and evaluation unit receives the data from the catheters and devices, and wherein the control and evaluation unit controls the catheters and devices for the detection of the data;
using high-resolution 3D-images, wherein the high-resolution 3D-images are recorded before the minimally-invasive intervention, and wherein the high-resolution 3D images are updated while the minimally-invasive intervention is carried out with current 3D data of the x-ray device,
wherein the system has a position determination device connected for an exchange of data to the control and evaluation unit for a determination of a three-dimensional position of one or more of the catheters in the space which are equipped with position sensors for detection of the three-dimensional position, wherein at least one catheter has at least two coils or antennas arranged at an angle to each other as position sensors, and
wherein a navigation device is connected for the exchange of data with the control mid evaluation unit for a magnetic navigation of one or more of the catheters, wherein the catheters have magnets for magnetic navigation using an external magnetic field generated by the navigation device.

15. The method as claimed in claim 13, wherein 4D image data is reconstructed from existing 3D image data by expansion with a timing sequence.

16. The method as claimed in claim 13, wherein no preoperative 3D image data is used.

17. The method as claimed in claim 13, wherein the system is used for carrying out and monitoring an intervention with a combination of an AcuNav catheter, a 3D ultrasound catheter or an OCT catheter.

18. The method as claimed in claim 13, wherein the system has an MPS position determination system.

19. A method of operating a system for carrying out and monitoring a minimally-invasive intervention:
providing the system having:
an x-ray device having an x-ray emitter and an x-ray detector,
a multi-axis articulated-arm robot, wherein the x-ray emitter and the x-ray detector are attached to at least one robotic arm of the multi-axis articulated-arm robot, wherein the x-ray emitter and the x-ray detector are moveable for recording images from different projection directions on a predetermined path around a patient support facility, and
a control and evaluation unit with interfaces for catheters and devices to be used for the minimally-invasive intervention, wherein the control and evaluation unit processes data selected from the group consisting of measurement data, image data and a combination thereof, wherein the control and evaluation unit receives the data from the catheters and devices, and wherein the control and evaluation unit controls the catheters and devices for the detection of the data;
inputting demographic data of a patient in a hospital information system;
transmitting the patient information to a high-resolution 3D examination unit;
recording and reconstruction of the high-resolution 3D images or datasets;
transmitting patient information data and high-resolution 3D datasets to the system;
recording and reconstruction of the high-resolution 3D images or datasets with the x-ray device, updating the high-resolution 3D images created before a procedure;
calibrating the ultrasound catheter with position sensors and registration with the available high-resolution 3D images;
introducing a ultrasound catheter under control, wherein the control comprises a combination of an x-ray control, a positioning system, and a location from at least 2 projections in an x-ray image wherein a navigation device is connected for the exchange of data with the control and evaluation unit for a magnetic navigation of one or more catheters, wherein the catheters have magnets for magnetic navigation using an external magnetic field generated by the navigation device;
updating the high-resolution 3D imaged with current 3D ultrasound data in a target area;
introducing a mapping catheter;
recording an intracardial ECG under control, wherein the control is selected from the group consisting of an x-ray control, a positioning system, a location from at least 2 projections in an x-ray image, and a combination thereof;
updating the available high-resolution 3D image with current 3D ultrasound data in the target area;
overlaying the mapping images with an anatomical image of heart chambers;
introducing a ablation catheter under control, wherein the control is selected from the group consisting of an x-ray control, a positioning system, a location from at least 2 projections in an x-ray image, and a combination thereof;
updating high-resolution 3D image with current 3D ultrasound data in the target area of the available high-resolution 3D image;
ablating selected tissue locations;
checking the ablation based upon a method selected from the group consisting of an OCT catheter use, a temperature measurement, a pressure measurement, a renewed mapping, and a combination thereof;
removing medical instruments and aids from the target area;
documentating and archiving the procedure in a Hospital Information system;
discharging the patient;
creating a bill; and
billing by the Hospital Information system.

* * * * *